United States Patent [19]
Frassica et al.

[11] Patent Number: 5,944,712
[45] Date of Patent: *Aug. 31, 1999

[54] CATHETER SIZE DESIGNATION SYSTEM

[75] Inventors: James J. Frassica, Chelmsford, Mass.; James F. Crittenden, Hollis, N.H.

[73] Assignee: Medtronic AVE, Inc., Santa Rosa, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/741,568

[22] Filed: Oct. 31, 1996

Related U.S. Application Data

[63] Continuation-in-part of application No. 08/150,766, Nov. 12, 1993, abandoned, which is a continuation of application No. 07/844,151, Mar. 2, 1992, abandoned.

[51] Int. Cl.⁶ .................................................. A61M 25/098
[52] U.S. Cl. ........................ 604/529; 604/523; 600/435; 600/434
[58] Field of Search ............................. 604/96, 264, 280, 604/282, 523; 128/657–658; 600/434, 435

[56] References Cited

U.S. PATENT DOCUMENTS

| | | | |
|---|---|---|---|
| 2,857,915 | 10/1958 | Sheridan | 128/349 |
| 3,529,633 | 9/1970 | Vaillancourt | 138/118 |
| 3,605,750 | 9/1971 | Sheridan et al. | 128/348 |
| 3,608,555 | 9/1971 | Greyson | 128/348 |
| 3,645,955 | 2/1972 | Flynn | 260/31.4 |
| 3,749,134 | 7/1973 | Slingluff et al. | 137/177 |
| 4,202,349 | 5/1980 | Jones | 128/689 |
| 4,323,071 | 4/1982 | Simpson et al. | 128/343 |
| 4,581,390 | 4/1986 | Flynn | 523/112 |
| 4,584,990 | 4/1986 | Haber et al. | |
| 4,834,726 | 5/1989 | Lambert | 604/281 |
| 5,000,484 | 3/1991 | Phelan et al. | 283/75 |
| 5,044,955 | 9/1991 | Jagmin | 433/229 |
| 5,045,071 | 9/1991 | McCormick et al. | 604/280 |
| 5,154,179 | 10/1992 | Ratner | 128/653.4 |
| 5,195,122 | 3/1993 | Fabian | 387/165 |
| 5,203,777 | 4/1993 | Lee | 604/280 |
| 5,289,831 | 3/1994 | Bosley | 128/899 |
| 5,320,100 | 6/1994 | Herweck et al. | 128/654 |
| 5,437,290 | 8/1995 | Bolger et al. | 128/898 |

OTHER PUBLICATIONS

Sherwood Prodcut Catalog, Sherwood Medical, 2 pages, Jul. 19, 1990.

*Primary Examiner*—Corrine McDermott
*Assistant Examiner*—Cris L. Rodriguez
*Attorney, Agent, or Firm*—Sterne, Kessler, Goldstein & Fox, P.L.L.C.

[57] ABSTRACT

The catheters in a family thereof in which each of the catheters has substantially the same configuration and adapted to perform the same function, but in which the catheters in the family differ from each other in at least one respect, are provided with radiographically distinguishable indicia by which each of the members of the family can be distinguished from the others by direct observation of its radiographic image.

27 Claims, 4 Drawing Sheets

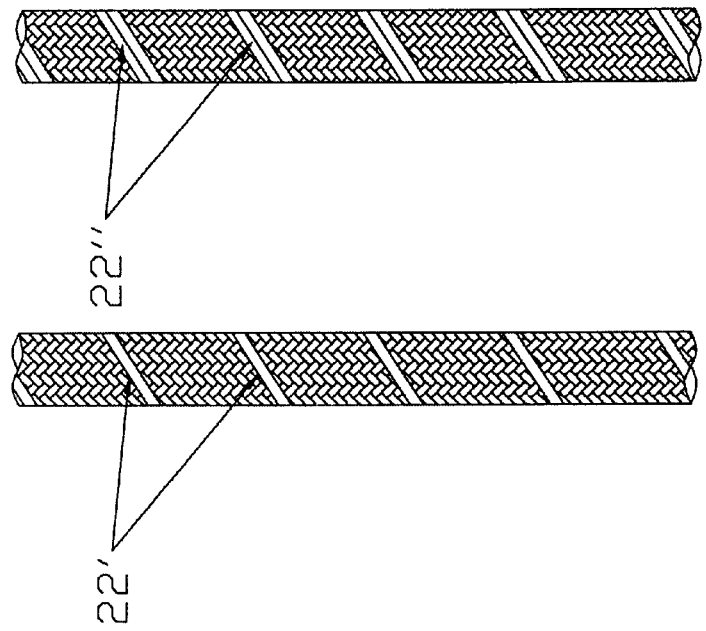
FIG 1B
FIG 1C
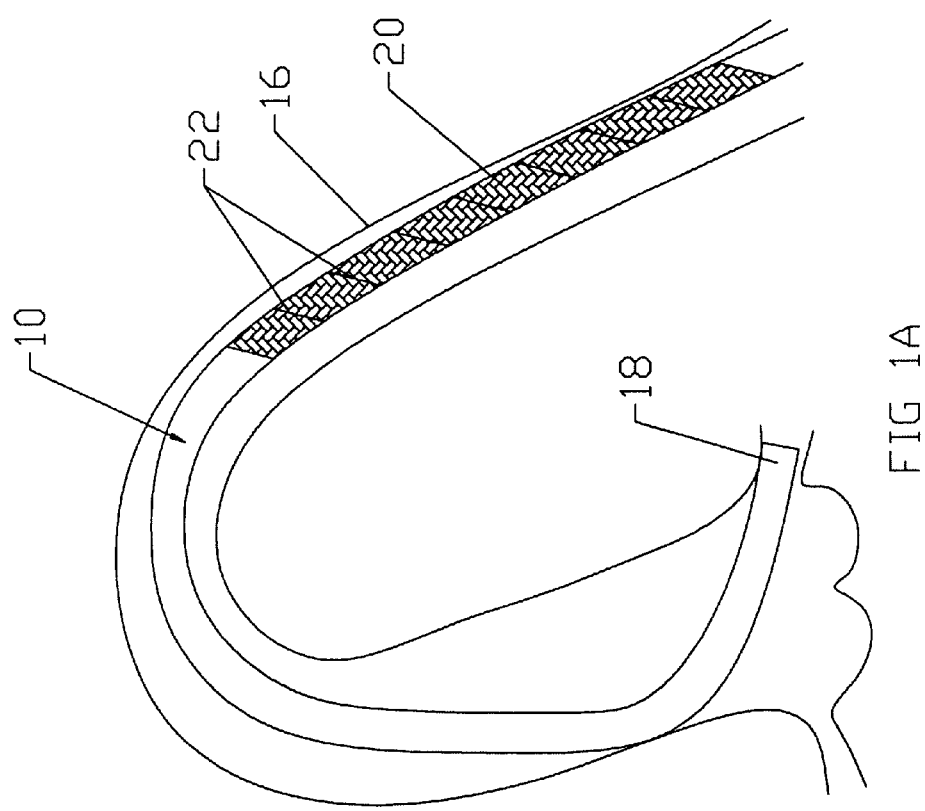
FIG 1A

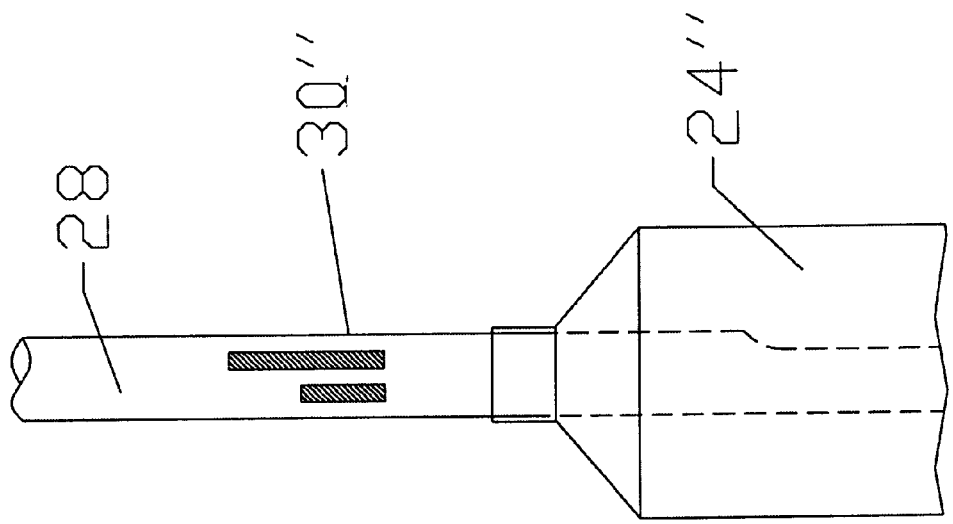
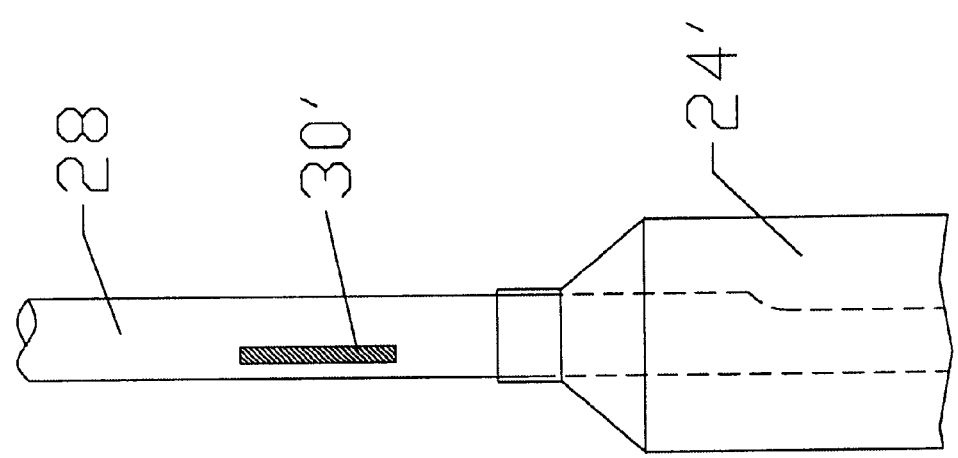
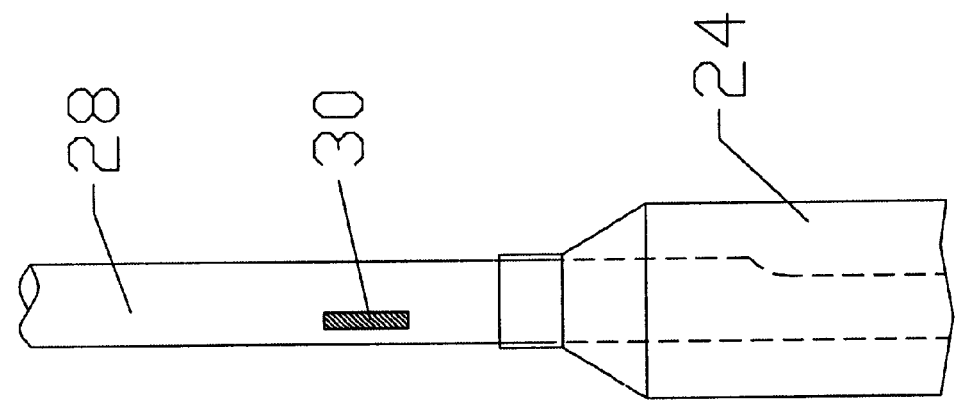

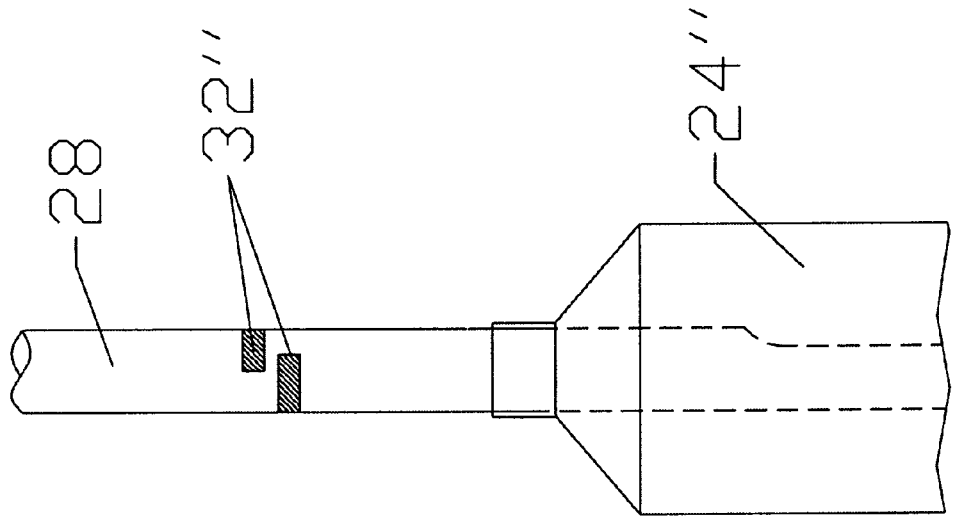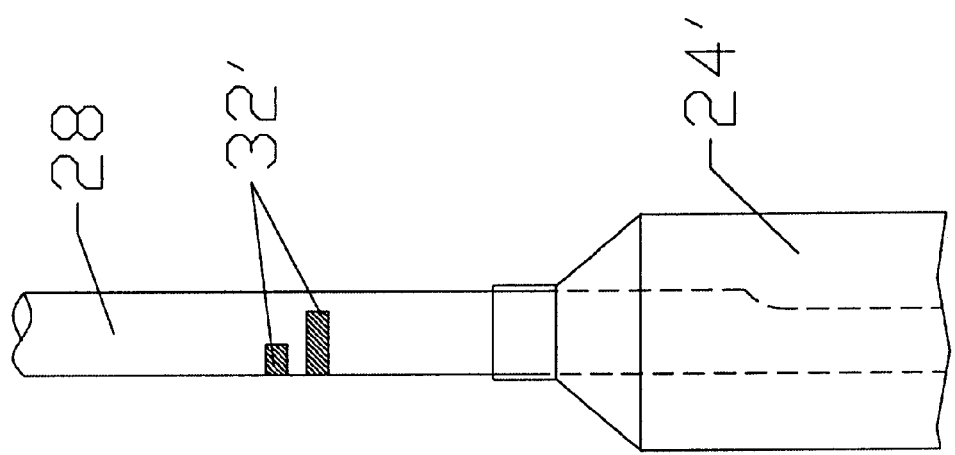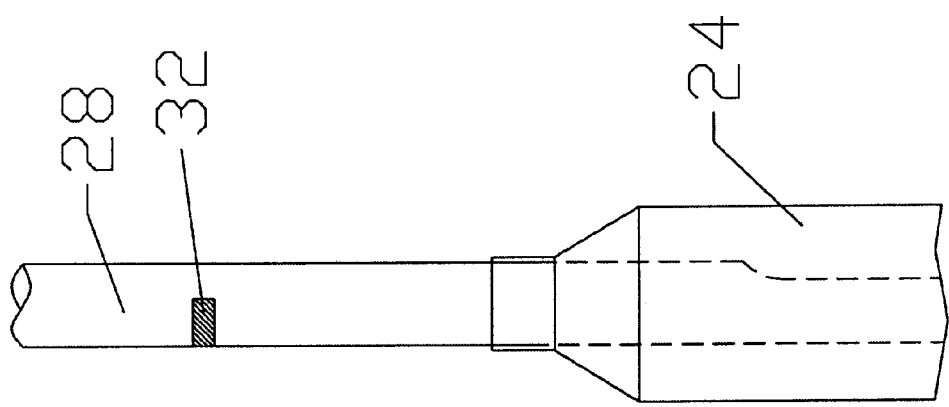

CATHETER SIZE DESIGNATION SYSTEM

CROSS REFERENCE TO RELATED APPLICATIONS

This application is a continuation in part of application Ser. No. 08/150,766, filed on Nov. 12, 1993 now abandoned, which is a continuation of application Ser. No. 07/844,151, filed on Mar. 2, 1992, now abandoned.

FIELD OF THE INVENTION

The invention relates to catheters adapted for use in medical procedures in which an x-ray image is made to record the catheterization procedure.

BACKGROUND OF THE INVENTION

Many catheterization procedures are performed in conjunction with x-ray techniques in order to monitor the position of the catheter, to facilitate guiding of the catheter as it is navigated through the patient's vasculature to diagnose diseases of the cardiovascular and vascular system and to observe the procedure as it progresses. A wide variety of catheters are used by cardiologists and interventional radiologists in procedures that are observed fluoroscopically and recorded on x-ray film. Such catheters typically come in various sizes, commonly denominated as "French" sizes, so that the physician can select the correct size of catheter for the patient. One "French" size corresponds to a dimension of approximately 0.013 inches in diameter.

The selection of the correct size of catheter for the patient and the procedure at hand is important. For example, in a catheter intended to be engaged with the ostium of a coronary artery (such as an angiographic catheter or an angioplasty guiding catheter) the correct selection of catheter diameter affects the manner in which the tip of the catheter will seat in the coronary ostium.

In heart catheterization procedures it is a common preliminary practice to conduct an angiographic study of the coronary anatomy. Typically that involves placement of an angiographic catheter in the heart with the tip of the catheter in engagement with one of the two coronary ostia leading to the coronary arteries. Radiopaque liquid then is injected into the coronary arteries and an cineangiogram is made to record that image. The angiogram so made then can be studied by the cardiologist or surgeon in order to determine a suitable therapeutic approach. Often the therapeutic approach may involve a subsequent catheterization procedure such as, for example, angioplasty.

In a typical angioplasty procedure a specially formed guide catheter is navigated from an insertion site in the groin, through the patient's arteries so that its tip is in engagement with the selected coronary ostium. A balloon dilatation catheter then is selected, in an appropriate size as determined by the physician, and is advanced through the guide catheter and into the coronary arteries. The balloon catheter typically will be associated with a guidewire which may be separate from or integral with the balloon catheter and which aids in navigation of the catheter through the coronary arteries. The catheter is manipulated to locate the balloon within the obstructing stenosis. The balloon then is inflated under high pressure to forcefully dilate the artery and open the lumen to increase blood flow through the artery.

Typically, the initial angiographic procedure is performed some time in advance of the angioplasty procedure and often may be performed by a different physician. Also of interest in connection with the present invention is the fact that in many instances it is necessary to perform a follow-up angioplasty procedure, for example, when restenosis develops. Restenosis develops in a substantial number of angioplasty patients and, when it does occur, it can occur from between several days to several months or longer after the initial angioplasty.

In follow-up angioplasty procedures as well as in the initial procedures it would be of significant benefit to the patient and the physician if the physician knew exactly what catheters had been used in the previous procedure whether diagnostic or therapeutic. Although an entry sometimes may be made in the patient's medical records, often such notes may not be made or, if made, may not be in sufficient detail to include the precise size of catheter that was used in the previous procedure. Although the physician will examine the patient's previous x-rays, if information concerning the details of the catheter that was used in the previous procedures is not readily available, such as in entries on the patient's record, the size of the catheter that was used cannot be determined accurately. The x-ray image is not sufficiently accurate to enable determination of the size of catheter used.

Knowledge by the physician as to the precise size of catheter used in the prior procedures would increase the probability of selection of the proper size catheter in the first instance. By selecting the proper size of catheter, the necessity for catheter exchanges may be avoided. Consequently, the total time of the procedure and extent of exposure of the patient to x-ray radiation may be maintained at a minimum.

It would be desirable, therefore, to provide a means by which a physician could determine readily from the patient's x-ray image, such as an angiogram, the size of catheter that was used in that x-ray procedure. It is among the general objects of the invention to provide such a system.

SUMMARY OF THE INVENTION

The invention relates to forming indicia on families of the same types of catheters such that different sizes of catheters in the family can be distinguished radiographically on the angiogram. Each of the catheters in the family is essentially identical, except for size, having the same functions as others in the family. Each catheter in the family is provided with a different radiopaque marker that will be clearly visible on the angiogram and which provides an indication of the size of the catheter. For example, a family of angiographic catheters, identical except for "French" size, can be provided with indicia indicative of the differences in size. Similarly, such indicia may be incorporated on a family of angioplasty catheters, such as angioplasty guide catheters or a family of angioplasty balloon catheters. In each instance, the radiopaque indicia provides an indication by which each of the catheters in the family can be distinguished from the other radiographically.

When using a catheter in the family constructed in accordance with the invention, the x-ray image on the angiogram will incorporate the radiopaque indicia thereby indicating the size of the catheter. Thus, when a physician (often a different physician) studies the x-ray in preparation for a subsequent or later follow-up procedure, it will be clear to the physician what catheter sizes were used. That enables the physician to better assess the size of catheter to be used in the follow-up procedure.

Various types of indicia can be used. One such arrangement may be used in connection with catheters having an internal braided layer. In such braided catheters different numbers of filaments that make up the braid can be formed from a highly radiopaque material so that different size catheters in such a family can be distinguished, one from the other, by the number of radiopaque filaments visible on the angiogram. Balloon catheters or other catheters that may not have a tubular braided layer may be provided with different numbers of radiopaque rings or bands on the catheter shaft to distinguish among various sizes of the same types of catheters that make up the family. Other radiopaque indicia may be used, such as various patterns of light and dark images, longitudinal stripes or embedded wires as well as combinations of such arrangements.

It is among the general objects of the invention to provide an improved system by which different size catheters in a family of catheters of the same type can be distinguished, one from the other under x-ray fluoroscopy.

Another object of the invention is to provide a system of the type described by which a physician can determine, from direct examination of an x-ray image, the size of catheter that was used.

A further object of the invention is to provide a system of the type described which enables the physician to better assess the size of catheter to use in a procedure.

BRIEF DESCRIPTION OF THE DRAWINGS

The foregoing and other objects and advantages of the invention will be appreciated more fully from the following further description thereof, with reference to the accompanying drawings wherein:

FIG. 1A illustrates, somewhat diagrammatically, an angiographic catheter in position in the aorta with the distal tip in engagement with the left coronary artery and showing the pattern of highly radiopaque indicia incorporated into the device;

FIGS. 1B and 1C are diagrammatic illustrations of portions of catheters of the same type as that shown in FIG. 1A and illustrating the pattern of distinguishing radiopaque indicia;

FIGS. 3A, 3B, and 3C illustrate diagrammatically, catheters in the same family that differ from each other only with respect to balloon size. FIGS. 3A, 3B, and 3C also illustrate the differentiating radiopaque indicia in the form of different length radiopaque stripes on the catheter shaft.

FIGS. 4A, 4B, and 4C illustrate diagrammatically, catheters in the same family that differ from each other only with respect to balloon size. FIGS. 4A, 4B, and 4C also illustrate the differentiating radiopaque indicia in the form of bands that partly encircle a portion of the catheter.

DESCRIPTION OF THE ILLUSTRATIVE EMBODIMENT

Figure 2C:
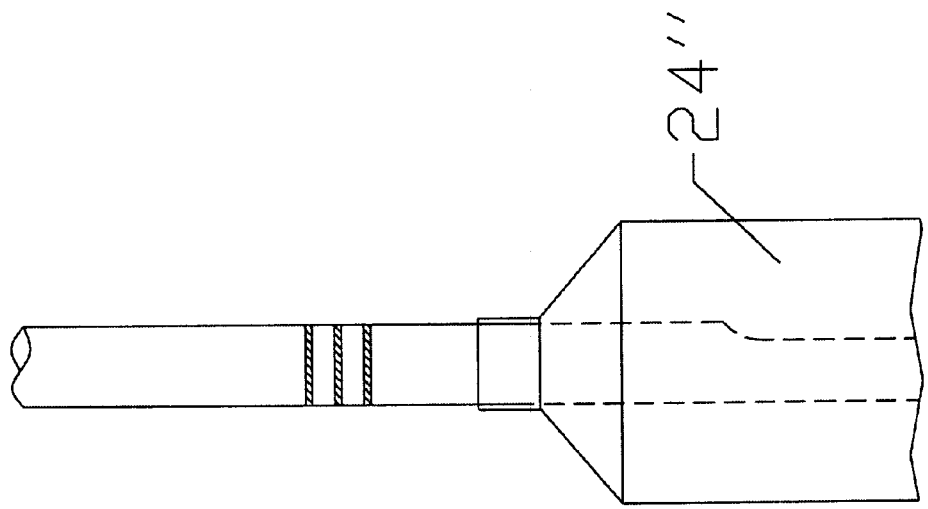
FIGS. 2B and 2C illustrate, diagrammatically, catheters in the same family as FIG. 2A that differ from each other only with respect to balloon size and illustrating the differentiating radiopaque indicia in the form of different numbers of radiopaque rings on the catheter shaft.

FIG. 1A illustrates, diagrammatically, a catheter, such as an angiographic catheter 10 adapted to delivery radiopaque contrast liquid to the region of the heart. As illustrated, the catheter 10 is in the form of a left coronary catheter adapted to engage the ostium 12 of the left coronary artery 14. As shown, the catheter 10 has a special curve formed at its distal end which is designed to facilitate engagement of the distal tip 18 of the catheter with the ostium when the device is advanced through the aorta 16 and over the aortic arch.

The angiographic catheter illustrated in FIG. 1A may embody a conventional well-known construction in which at least a substantial portion of the length of the catheter shaft is reinforced internally by a braid 20. The braid 20 may be formed from metallic or polymeric filaments. Illustrative of such type of braided catheter construction is U.S. Pat. No. 3,485,234.

In accordance with the invention, the catheter is provided with radiopaque indicia. In the embodiment illustrated in FIG. 1A, the indicia may take the form of a single helical stripe 22. The stripe 22 may be formed by selecting a highly radiopaque material, such as a gold alloy, for one of the filaments in the braid.

FIGS. 1B and 1C illustrate sections of an identical type of catheter (i.e., a catheter in the same "family") but with distinguishable radiopaque indicia. As illustrated in FIG. 1B a double stripe 22' is provided and in FIG. 1C, a triple stripe 22". In accordance with the invention the distinguishing indicia are used to distinguish the different sizes of the catheters. For example, in the illustrative embodiment, the number of stripes plus five may be used to indicate the "French" size of the catheter. Thus, the angiographic catheter illustrated in FIG. 1 may be a six "French" catheter, the indicia illustrated in FIG. 1B a seven "French" catheter and a catheter with the three-stripe indicia in FIG. 1C, an eight "French" catheter. In this manner, a physician can examine the previously taken x-ray and determine the size of the catheter that was used, thereby providing an indication of the size of the artery that may be expected.

Figure 2B:
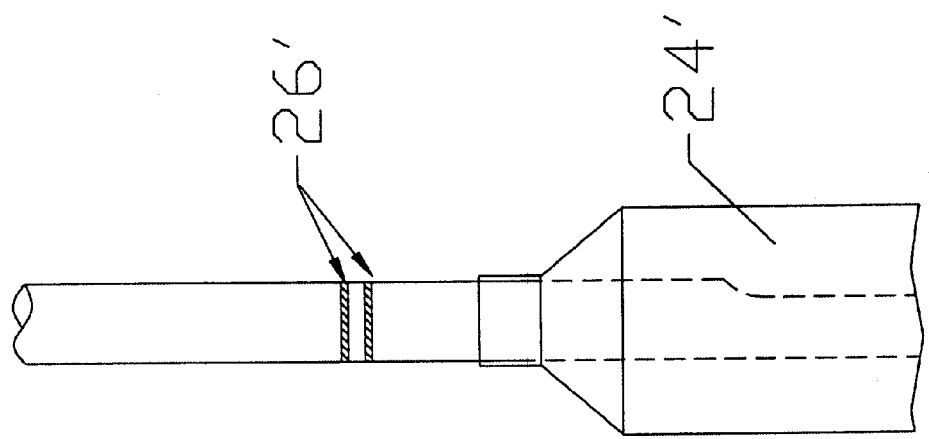
Figure 2A:
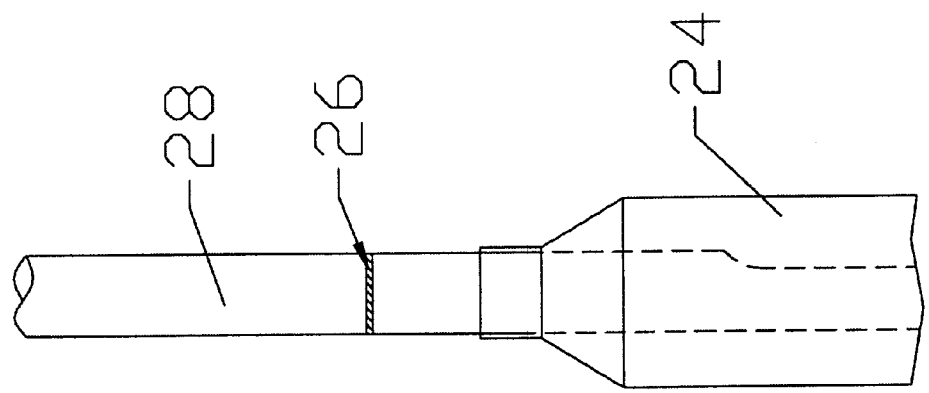
FIG. 2A is a diagrammatic illustration of a balloon dilatation catheter in which ring-type of radiopaque indicia is used.

Similar techniques may be employed in connection with other catheters, such as balloon dilatation catheters like portions of which are illustrated diagrammatically in FIGS. 2A–C. Among the principal distinguishing features of such balloon dilatation catheters is the size of the balloon 24. In accordance with the invention, catheters having different size balloons (e.g., 24, 24', 24") of the same type of catheter may be distinguished one from the other by different radiopaque indicia on the catheter. In the illustrative embodiment of FIGS. 2A, 2B and 2C, catheters may be distinguished by highly radiopaque gold bands 26 attached to the catheter shaft 28. For example, in FIG. 2A, the single gold band 26 may signify a balloon catheter in which the balloon has a diameter of 1.5 millimeters. A balloon dilatation catheter having two bands 26 (FIG. 2B) may have a 2.0 millimeter diameter balloon 24'. The three-band (26") embodiment illustrated in FIG. 2C may signify a balloon 24" having a 2.5 millimeter diameter.

The foregoing are meant to be illustrative examples only. Other distinguishing indicia may be employed, such as differentiation in the degree of radiopacity so as to provide varying light and dark distinguishing indicia. Other indicia such as longitudinal stripes, 30, 30', and 30" (FIGS. 3A, 3B, 3C) and split radiopaque bands, 32, 32' and 32" (FIGS. 4A, 4B and 4C) that partly encircle a portion of the catheter as well as various combinations thereof, may be employed.

Thus, it will be appreciated that the invention provides a means by which a physician can determine directly from an examination of the patient's x-ray certain characteristics of a catheter used in a previous procedure. That information enables the physician to better assess the specific catheter selected for the procedure at hand.

It should be understood that the foregoing description of the invention is intended merely to be illustrative thereof and that other embodiments, modifications and equivalents may be apparent to those skilled in the art without departing from its spirit.

Having thus described the invention that we desire to claim and secure by Letters Patent is:

1. A family of radiographically distinguishable catheters comprising:

a plurality of catheters having substantially the same configuration, the catheters in the family differing from each other in at least one respect;

a coded self-referencing pattern of radiographically distinguishable radiopaque indicia associated with each catheter in the family, the indicia on each catheter in the family being different than the indicia on other catheters in the family, the identity of an individual catheter in the family being unique and readily determinable by observing a radiographic image of that catheter.

2. The family of catheters as defined in claim 1 wherein said catheters include in their structure a braided tubular element formed from a plurality of helically arranged filaments extending along the length of the catheter, the family of catheters including catheters with different dimensions;

said radiographically distinguishable radiopaque indicia comprising at least one filament in each catheter in the family being formed from a highly radiopaque material that is radiographically visible, the catheters with different dimensions in the family of catheters having different numbers of said radiopaque filaments.

3. The family of radiographically distinguishable catheters as defined in claim 1 wherein the at least one respect is a size of a catheter.

4. The family of radiographically distinguishable catheters as defined in claim 1 wherein the identity of an individual catheter in the family of catheters may be readily determined by observation of a radiographic image of that catheter without reference to any dimension of the radiographic image.

5. The family of radiographically distinguishable catheters as defined in claim 1 wherein the size of the self-referencing pattern of radiographically distinguishable radiopaque indicia is independent of any physical dimension of an individual catheter in the family of catheters.

6. The family of radiographically distinguishable catheters as defined in claim 1 wherein the size of the self-referencing pattern of radiographically distinguishable radiopaque indicia is independent of a size of an individual catheter in the family of catheters.

7. The family of catheters of claim 1 whereby the respect in which the catheters in the family differs comprises at least one dimension of the catheter.

8. The family of catheters as defined in claim 1 in which the catheters differ dimensionally from each other and wherein said radiographically distinguishable radiopaque indicia comprises radiopaque bands carried by the catheters, dimensionally different of said catheters having radiographically distinguishable bands.

9. The family of catheters as defined in claim 8 wherein at least some of said radiopaque bands completely encircle the catheter shaft.

10. The family of catheters as defined in claim 8 wherein at least some of said radiopaque bands partly encircle a portion of the catheter.

11. The family of catheters as defined in claim 1 wherein said radiographically distinguishable indicia comprises stripes formed on a catheter, the stripes of different catheters in the family being of different lengths.

12. The family of catheters as defined in any one of claims 1, 2, 8–11 wherein the catheters in the family comprise guide catheters.

13. The family of catheters as defined in any one of claims 1, 2, 8–11 wherein the catheters in the family comprise balloon catheters.

14. In a family of catheters, the individual catheters in the family having substantially the same configuration, and differing from each other in at least one respect, a coding system for distinguishing among the individual catheters in the family comprising:

a coded self-referencing pattern of radiographically distinguishable radiopaque indicia disposed upon each individual catheter in the family;

the indicia disposed upon each individual catheter in the family being different than the indicia disposed upon other individual catheters in the family;

the indicia being indicative of the at least one differing respect of an individual catheter in the family;

the differing respect of an individual catheter in the family being unique and readily determinable by observing a radiographic image of that catheter.

15. In a family of catheters as defined in claim 14, wherein said catheters include in their structure a braided tubular element formed from a plurality of helically arranged filaments extending along the length of the catheter;

said self-referencing pattern of radiographically distinguishable radiopaque indicia comprising at least one filament in each catheter in the family being formed from a highly radiopaque material that is radiographically visible, the catheters in the family of different respects having different numbers of said radiopaque filaments.

16. The coding system as defined in claim 14 wherein the identity of an individual catheter in the family of catheters may be readily determined by observation of a radiographic image of that catheter without reference to any dimension of the radiographic image.

17. The coding system as defined in claim 14 wherein the size of the self-referencing pattern of radiographically distinguishable radiopaque indicia is independent of any physical dimension of an individual catheter in the family of catheters.

18. The coding system as defined in claim 14 wherein the size of the self-referencing pattern of radiographically distinguishable radiopaque indicia is independent of a size of an individual catheter in the family of catheters.

19. A system for identifying catheters comprising:

a family of catheters, the individual catheters in the family having substantially the same configuration, and differing from each other in at least one respect; and a coding system comprising:

a coded self-referencing pattern of radiographically distinguishable radiopaque indicia disposed upon each individual catheter in the family;

the indicia disposed upon each individual catheter in the family being different than the indicia disposed upon other individual catheters in the family;

the indicia being indicative of the at least one differing respect of an individual catheter in the family;

the differing respect of an individual catheter in the family being unique and readily determinable by observing a radiographic image of that catheter.

20. The system as defined in claim 19 wherein the catheters in the family comprise guiding catheters.

21. The system as defined in claim 19 wherein the catheters in the family comprise balloon catheters.

22. The system as defined in claim 19 wherein the at least one respect is a size of a catheter.

23. The system as defined in claim 19 wherein the identity of an individual catheter in the family of catheters may be readily determined by observation of a radiographic image of that catheter without reference to any dimension of the radiographic image.

24. The system as defined in claim 19 wherein the size of the self-referencing pattern of radiographically distinguishable radiopaque indicia is independent of any physical dimension of an individual catheter in the family of catheters.

25. The system as defined in claim 19 wherein the size of the self-referencing pattern of radiographically distinguishable radiopaque indicia is independent of a size of an individual catheter in the family of catheters.

26. A catheter that is one of a family of a plurality of catheters having substantially the same configuration, said individual catheter differing from the other catheters in the family in at least one respect, each of the catheters in the family having a pattern of radiographical distinguishable radiopaque indicia, said catheter comprising:

a pattern of radiographic indicia on said individual catheter being different than the radiographic indicia on the other catheters in the family, said difference in the indicia providing a coded self-referencing radiographically distinguishable pattern by which the identity of the individual catheter can be readily determined by observing a radiographic image of that individual catheter.

27. The coding system as defined in claim 16 wherein the respect in which an individual catheter differs from other catheters in the family comprises a dimensional characteristic of said individual catheter.

* * * * *